(12) United States Patent
Shealy et al.

(10) Patent No.: US 7,645,226 B2
(45) Date of Patent: Jan. 12, 2010

(54) RELAXATION DEVICE AND METHOD

(75) Inventors: C. Norman Shealy, Fair Grove, MO (US); Gabor Lederer, Paterson, NJ (US)

(73) Assignee: Biogenics II L.L.C., Fair Grove, MO (US)

(*) Notice: Subject to any disclaimer, the term of this patent is extended or adjusted under 35 U.S.C. 154(b) by 1142 days.

(21) Appl. No.: 10/988,204

(22) Filed: Nov. 12, 2004

(65) Prior Publication Data
US 2006/0106276 A1 May 18, 2006

(51) Int. Cl.
*A61M 21/00* (2006.01)
(52) U.S. Cl. ........................................ 600/27
(58) Field of Classification Search .......... 600/26–28; 128/897
See application file for complete search history.

(56) References Cited

U.S. PATENT DOCUMENTS

| | | | |
|---|---|---|---|
| 4,315,502 A | 2/1982 | Gorges | |
| 4,858,609 A | 8/1989 | Cole | |
| 4,892,106 A * | 1/1990 | Gleeson, III | 600/28 |
| 4,902,274 A | 2/1990 | Gleeson, III | |
| 5,037,376 A * | 8/1991 | Richmond et al. | 600/26 |
| 5,047,006 A | 9/1991 | Brandston et al. | |
| 5,242,376 A | 9/1993 | Shealy et al. | |
| 5,518,497 A | 5/1996 | Widjaja et al. | |
| 5,577,990 A | 11/1996 | Widjaja et al. | |
| 5,599,274 A | 2/1997 | Widjaja et al. | |
| 5,643,173 A | 7/1997 | Welles | |
| 5,709,645 A | 1/1998 | Siever | |
| 5,896,457 A | 4/1999 | Tyrrel | |
| 6,299,632 B1 | 10/2001 | Jaillet | |
| 6,443,977 B1 | 9/2002 | Jaillet | |
| 6,902,296 B2 * | 6/2005 | Searfoss, III | 362/231 |

OTHER PUBLICATIONS

C. Norman Shealy, M.D., et al., "Effects of Color Photostimulation Upon Neurochemicals and Neurohormones," J. Neurol. Orthop. Med. Surg. vol. 17, No. 1, 1996, pp. 95-96.

* cited by examiner

*Primary Examiner*—Charles A Marmor, II
*Assistant Examiner*—Christine D Hopkins
(74) *Attorney, Agent, or Firm*—Foley & Lardner LLP

(57) ABSTRACT

A device for inducing a relaxation state in a user is provided. The device includes a pair of light sources directed toward a user's eye. The two light sources emit different colors, preferably blue and red. A second pair of light sources may be directed toward the user's other eye. The user can adjust both the color level and the brightness emitted by the pair of lights. The user further may control a flash frequency of the light emitted by the pair of lights. Additionally, the user may control the time duration of the relaxation session. Preferably, the relaxation device is portable. Preferably, the relaxation device is mounted in a pair of eyeglasses or in a mask and includes control electronics for controlling the light sources and a power source for powering the lights and the control electronics.

8 Claims, 10 Drawing Sheets

RELAXATION DEVICE AND METHOD

FIELD OF THE INVENTION

The present invention relates generally to the field of relaxation devices and methods and particularly to relaxation devices that use flashes of light.

BACKGROUND OF THE INVENTION

Prior art relaxation devices that affect the mood of a subject by directing light at the eyes of the subject are known. The light may be continuous or may be flashing at different frequencies. Additionally, the light may be colored. The duration of time that the light is emitted from the device as well as the speed at which the light flashes may be set by the subject. The subject places the relaxation device such that the device covers the eyes, the subject closes his or her eyes, and light emitted from the device is directed at the subject's eyes. After a period of time, the subject enters a relaxed mood state. These mood states are known as alpha, beta, delta and theta, and correspond to different levels of consciousness and awareness. Examples of these devices, as well as an explanation of the mood state, are disclosed in U.S. Pat. Nos. 3,722,501; 4,315,502; 4,388,928; 4,777,937; 4,858,609; 5,047,006; 5,242,376. These prior devices are generally limited in their ability to allow the user to control the color separately from the brightness.

SUMMARY OF THE INVENTION

An exemplary embodiment of the invention relates to a device for inducing a relaxation state in a user. The device includes a first light source, a second light source adjacent the first light source, a first color control, a second color control, and a brightness control. The first light source emits a first light beam having a first color toward a first eye of a user. The first light beam is generated using a first amplitude modulated signal. The second light source emits, simultaneous with the first light source, a second light beam having a second color toward the first eye of the user. The second light beam is generated using a second amplitude modulated signal. The second color is different from the first color. The first color control provides user selection of the pulse width of a first rectangular wave. The second color control provides user selection of the pulse width of a second rectangular wave. The brightness control provides user variation of the repetition rate of the first rectangular wave thereby forming the first amplitude modulated signal and provides user variation of the repetition rate of the second rectangular wave thereby forming the second amplitude modulated signal. The first light beam and the second light beam provide a first combined color perceived by the first eye of the user. The first color control and the second color control provide user control of the first combined color, and the brightness control provides user control of the brightness of the first combined color.

In an exemplary embodiment, the separation distance between the first light source and the second light source is in the range of approximately 3 to approximately 4 millimeters. Preferably, the first color is red and the second color is blue. The pulse width of the first rectangular wave and the pulse width of the second rectangular wave are in the range from approximately 62.5 microseconds to approximately 500 microseconds in an exemplary embodiment.

In an exemplary embodiment, the device further includes a third light source and a fourth light source adjacent the third light source. The third light source emits a third light beam having a third color toward a second eye of the user. The third light beam is generated using the first amplitude modulated signal. The fourth light source emits, simultaneous with the third light source, a fourth light beam having a fourth color toward the second eye of the user. The fourth light beam is generated using the second amplitude modulated signal. The fourth color is different from the third color. The third light beam and the fourth light beam provide a second combined color perceived by the second eye of the user. The first color control and the second color control provide user control of the second combined color, and the brightness control provides user control of the brightness of the second combined color. In an exemplary embodiment, the separation distance between the third light source and the fourth light source is in the range of approximately 3 to approximately 4 millimeters. Preferably, the third color is red and the fourth color is blue.

In an exemplary embodiment, the device further includes a session duration control. The session duration control allows user selection of the session duration in the range from approximately 20 minutes to approximately 60 minutes. In an exemplary embodiment, the device further includes a flash frequency control. The flash frequency control allows user selection of the flash frequency of the first combined color and the second combined color in the range from approximately 1 hertz to approximately 7.5 hertz.

Another exemplary embodiment of the invention relates to a device for inducing a relaxation state in a user. The device includes a surface, a light emitting apparatus coupled to the surface, and a power source coupled to the light emitting apparatus that provides power to the light emitting apparatus. The light emitting apparatus includes a first light source, a second light source adjacent the first light source, a first color control, a second color control, and a brightness control. The first light source emits a first light beam having a first color toward a first eye of a user. The first light beam is generated using a first amplitude modulated signal. The second light source emits, simultaneous with the first light source, a second light beam having a second color toward the first eye of the user. The second light beam is generated using a second amplitude modulated signal. The second color is different from the first color. The first color control provides user selection of the pulse width of a first rectangular wave. The second color control provides user selection of the pulse width of a second rectangular wave. The brightness control provides user variation of the repetition rate of the first rectangular wave thereby forming the first amplitude modulated signal and provides user variation of the repetition rate of the second rectangular wave thereby forming the second amplitude modulated signal. The first light beam and the second light beam provide a first combined color perceived by the first eye of the user. The first color control and the second color control provide user control of the first combined color, and the brightness control provides user control of the brightness of the first combined color.

In an exemplary embodiment, the separation distance between the first light source and the second light source is in the range of approximately 3 to approximately 4 millimeters. Preferably, the first color is red and the second color is blue. The pulse width of the first rectangular wave and the pulse width of the second rectangular wave are in the range from approximately 62.5 microseconds to approximately 500 microseconds in an exemplary embodiment.

In an exemplary embodiment, the light emitting apparatus further includes a third light source and a fourth light source adjacent the third light source. The third light source emits a third light beam having a third color toward a second eye of the user. The third light beam is generated using the first amplitude modulated signal. The fourth light source emits, simultaneous with the third light source, a fourth light beam having a fourth color toward the second eye of the user. The fourth light beam is generated using the second amplitude modulated signal. The fourth color is different from the third color. The third light beam and the fourth light beam provide a second combined color perceived by the second eye of the user. The first color control and the second color control provide user control of the second combined color, and the brightness control provides user control of the brightness of the second combined color. In an exemplary embodiment, the separation distance between the third light source and the fourth light source is in the range of approximately 3 to approximately 4 millimeters. Preferably, the third color is red and the fourth color is blue.

In an exemplary embodiment, the light emitting apparatus further includes a session duration control. The session duration control allows user selection of the session duration in the range from approximately 20 minutes to approximately 60 minutes. In an exemplary embodiment, the light emitting apparatus further includes a flash frequency control. The flash frequency control allows user selection of the flash frequency of the first combined color and the second combined color in the range from approximately 1 hertz to approximately 7.5 hertz.

Another exemplary embodiment of the invention relates to a method of inducing a relaxation state in a user. The method includes receiving a first input from a first color control, wherein the first color control provides user selection of the pulse width of a first rectangular wave; receiving a second input from a second color control, wherein the second color control provides user selection of the pulse width of a second rectangular wave; receiving a second input from a brightness control, wherein the brightness control provides user variation of the repetition rate of the first rectangular wave thereby forming a first amplitude modulated signal and provides user variation of the repetition rate of the second rectangular wave thereby forming a second amplitude modulated signal; emitting a first light beam from a first light source toward a first eye of a user, the first light beam having a first color and generated from the first amplitude modulated signal; emitting, simultaneous with the first light beam, a second light beam from a first light source toward the first eye of the user, the second light beam having a second color and generated from the second amplitude modulated signal, wherein the second color is different from the first color; and providing a first combined color perceived by the first eye of the user from the first light beam and the second light beam wherein the first color control and the second color control provide user control of the first combined color, and the brightness control provides user control of the brightness of the first combined color.

The method may further include emitting a third light beam from a third light source toward a second eye of the user, the third light beam having a third color and generated from the first amplitude modulated signal; emitting, simultaneous with the third light beam, a fourth light beam from a fourth light source toward the second eye of the user, the fourth light beam having a fourth color and generated from the second amplitude modulated signal, wherein the fourth color is different from the third color; and providing a second combined color perceived by the second eye of the user from the third light beam and the fourth light beam wherein the first color control and the second color control provide user control of the second combined color, and the brightness control provides user control of the brightness of the second combined color.

In an exemplary embodiment, the separation distance between the first light source and the second light source is in the range of approximately 3 to approximately 4 millimeters. In an exemplary embodiment, the separation distance between the third light source and the fourth light source is in the range of approximately 3 to approximately 4 millimeters. Preferably, the first color is red and the second color is blue. Preferably, the third color is red and the fourth color is blue. The pulse width of the first rectangular wave and the pulse width of the second rectangular wave are in the range from approximately 62.5 microseconds to approximately 500 microseconds in an exemplary embodiment.

Further objects, features, and advantages of the invention will be apparent from the following detailed description when taken in conjunction with the accompanying drawings.

BRIEF DESCRIPTION OF THE DRAWINGS

The exemplary embodiments will hereafter be described with reference to the accompanying drawings, wherein like numerals will denote like elements.

DETAILED DESCRIPTION OF THE INVENTION

Figure 1:
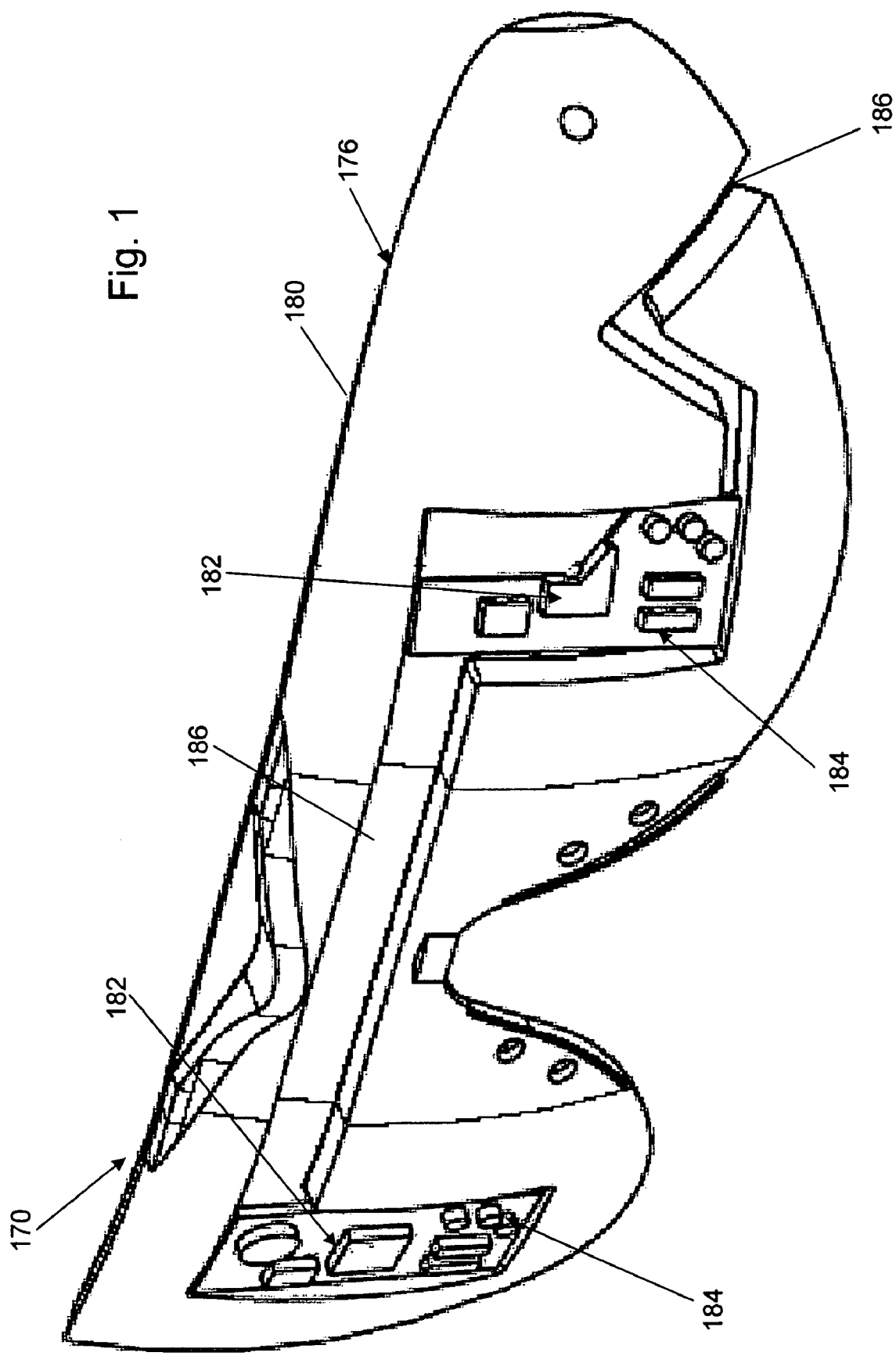
FIG. 1 is a front perspective view of a relaxation device in accordance with an exemplary embodiment of the invention.

With reference to FIG. 1, a relaxation device 170 in accordance with the invention comprises a left portion, a right portion, and an eye covering portion 176. Preferably, the left portion connects to the eye covering portion 176 near a first edge and allows the relaxation device 170 to rest on the left ear of a user. Similarly, the right portion connects to the eye covering portion 176 near a second edge opposite the first edge and allows the relaxation device 170 to rest on the right ear of the user. The left portion and the right portion allow the mounting of the relaxation device 170 to the head of a user thereby covering the eyes of the user with the eye covering portion 176.

The eye covering portion 176 comprises, an eye mask 180, an LED arrangement 182, control electronics 184, and a cable channel 186. The control electronics 184 and the LED arrangement 182 attach to the eye mask 180. A power source may connect to the eye covering portion 176 through a first cable mounted in the cable channel 186. In alternative embodiments, the power source may mount to the eye covering portion 176. In alternative embodiments, some of the control electronics may not mount to the eye covering portion 176 and instead may connect to the eye covering portion 176 through a second cable mounted in the cable channel 186. The first cable and the second cable may be integral with or separate from each other.

The power source provides electrical power to operate all of the control electronics that turn the LED arrangement 182 on and off. In an exemplary embodiment, all of the control electronics can operate using approximately three volts of electricity. The three volts, preferably, is provided using two AA batteries connected in series.

The eye mask 180 is shaped to block light not originating from the LED arrangement 182 from reaching the user's eyes when the device 170 is placed on the head of the user. The eye mask 180 may be manufactured from a variety of materials including but not limited to, plastic, metal, cloth, etc. The eye mask 180 may have different sizes to comfortably accommodate the different size heads and the different eye spacing of users.

In an exemplary embodiment, the LED arrangement 182 includes a first pair of LEDs adjacent the left eye of the user and a second pair of LEDs adjacent the right eye of the user when the relaxation device 170 is mounted for use. Preferably, each pair of LEDs includes an LED that emits a red light beam and an LED that emits a blue light beam. Color is the perceptual result of light in the visible region of the spectrum incident upon the retina of the human eye. Using separate color and brightness controls to generate signals that drive each LED, as related below, the user can adjust the color of the light beam perceived by each eye along the color spectrum from red to blue with a purple light beam perceived using a combination of the red and blue light beams emitted from the LED arrangement 182. A combined light beam is perceived by the user whether or not the red and blue light beams actually combine physically. Purple cannot be produced by a single wavelength, but must be produced as a mixture of shortwave and longwave light. Purple on a chromaticity diagram joins extreme blue to extreme red.

Preferably, the LED emitting the red light beam is lateral to the LED emitting the blue light beam. In an exemplary embodiment, the LEDs in each pair of LEDs are separated from each other in the range of approximately 3 to approximately 4 millimeters. In alternative embodiments, the LEDs in each pair may be offset from each other along any diameter of a circle having a diameter in the range of approximately 3 to approximately 4 millimeters. Each pair of LEDs generally is arranged on the eye mask 180 in front of either the left eye or the right eye of the user when the eye covering portion 176 is mounted for use to the head of the user.

Using color controls, the relaxation device 170 allows a user to control the color of the light beams produced by the LED arrangement 182 as perceived by a user of the relaxation device 170. In an exemplary embodiment, the LEDs emitting the red light beam are adjusted simultaneously using a single control, and the LEDs emitting the blue light beam also are adjusted simultaneously using a single control. As perceived by the eyes of the user, the red and blue light beams emitted by the LEDs combine to form a third color that is visible to the user. The control electronics 184 generate amplitude modulated signals that are sent to the LED arrangement 182. By modifying the amplitude modulated signal, the color of the light beam as perceived by the user of the relaxation device 170 can be controlled.

In an exemplary embodiment, the color control provides eight color levels to each LED of the LED arrangement 182. Thus, each color level comprises 12.5% of the maximum color level. In an exemplary embodiment, the first color level is provided by a 62.5 µs amplitude modulated signal in the form of a rectangular wave. The maximum color level is provided by an amplitude modulated signal comprised of eight consecutive 62.5 µs impulses resulting in a 500 µs pulse width (8*62.5 µs) for full color. A matrix of different color levels can be formed by independently adjusting the LEDs emitting the red light beam from 62.5 µs to 500 µs in pulse width and the LEDs emitting the blue light beam from 62.5 µs to 500 µs in pulse width.

Figure 2:
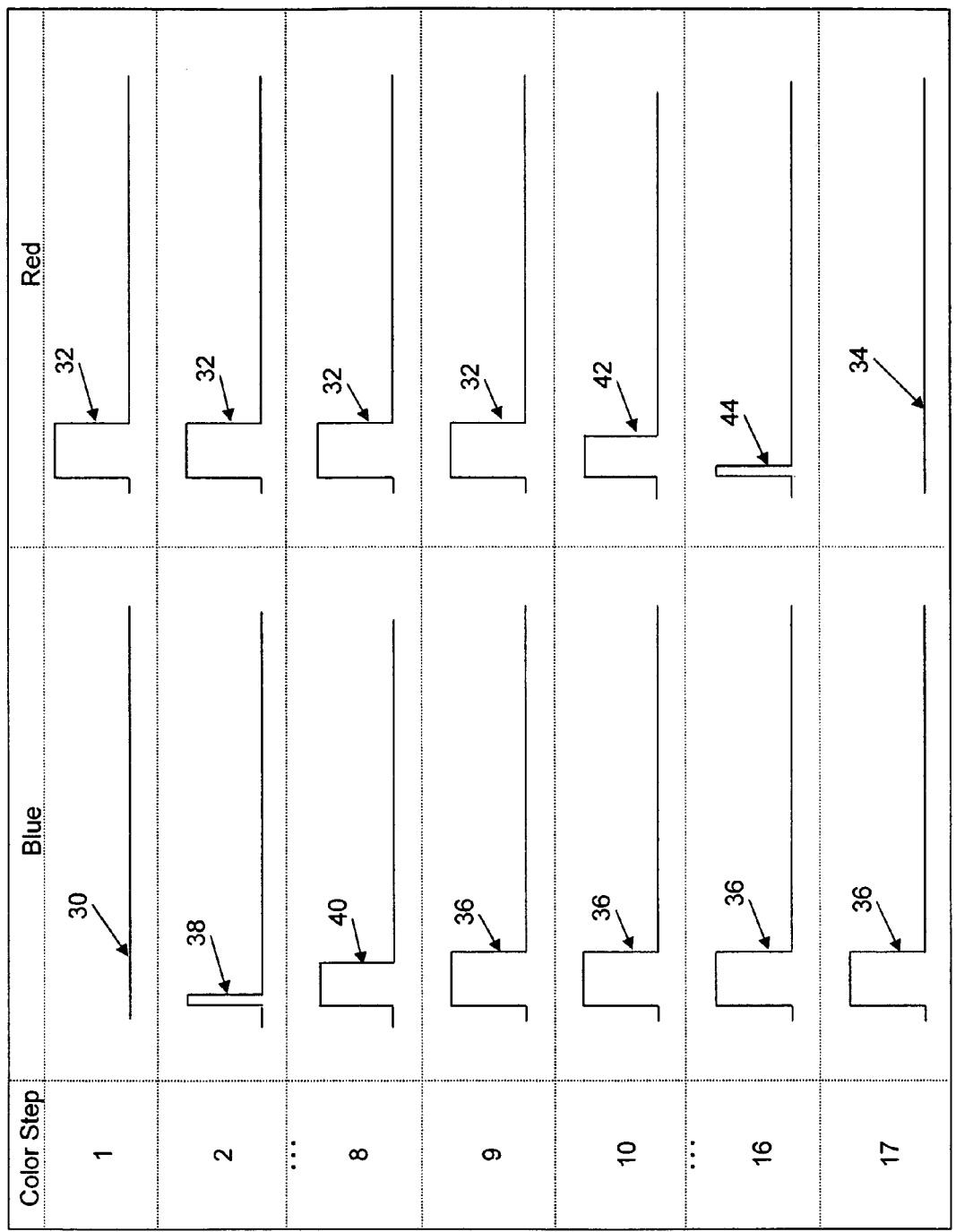
FIG. 2 illustrates the sequence of modulated signal waveforms that provide different colors as perceived by a user of the relaxation device in accordance with an exemplary embodiment.

Using the combination of two LEDs emitting different color levels, the color perceived by the user can be sequentially adjusted to form 17 different color steps where one or the other of the LEDs is at 100%. As illustrated in FIG. 2, the color perceived by the user can be adjusted from zero blue 30 and full red 32 (500 µs pulse width signal to the LED 18, 22) at step 1 to zero red 34 and full blue 36 (500 µs pulse width signal to the LED 20, 24) at step 17. At step 1, the color of the light beam visible to the user is 0% blue 30 (off) and 100% red 32. Thus, at step 1, the user perceives a red color level. At step 2, the color of the light beam visible to the user is 12.5% blue 38 (62.5 µs pulse width signal to the LED 20, 24) and 100% red 32. At step 8, the color of the light beam visible to the user is 87.5% blue 40 (437.5 µs pulse width signal to the LED 20, 24) and 100% red 32. At step 9, the color of the light beam visible to the user is 100% red 32 and 100% blue 36. Thus, at step 9, the user perceives a purple color level. At step 10, the color of the light beam visible to the user is 100% blue 36 and 87.5% red 42 (437.5 µs pulse width signal to the LED 18, 22). At step 16, the color of the light beam visible to the user is 100% blue 36 and 12.5% red 44 (62.5 µs pulse width signal to the LED 18, 22). At step 17, the color of the light beam visible to the user is 0% red 34 (off) and 100% blue 36. Thus, at step 17, the user perceives a blue color level.

Figure 3:
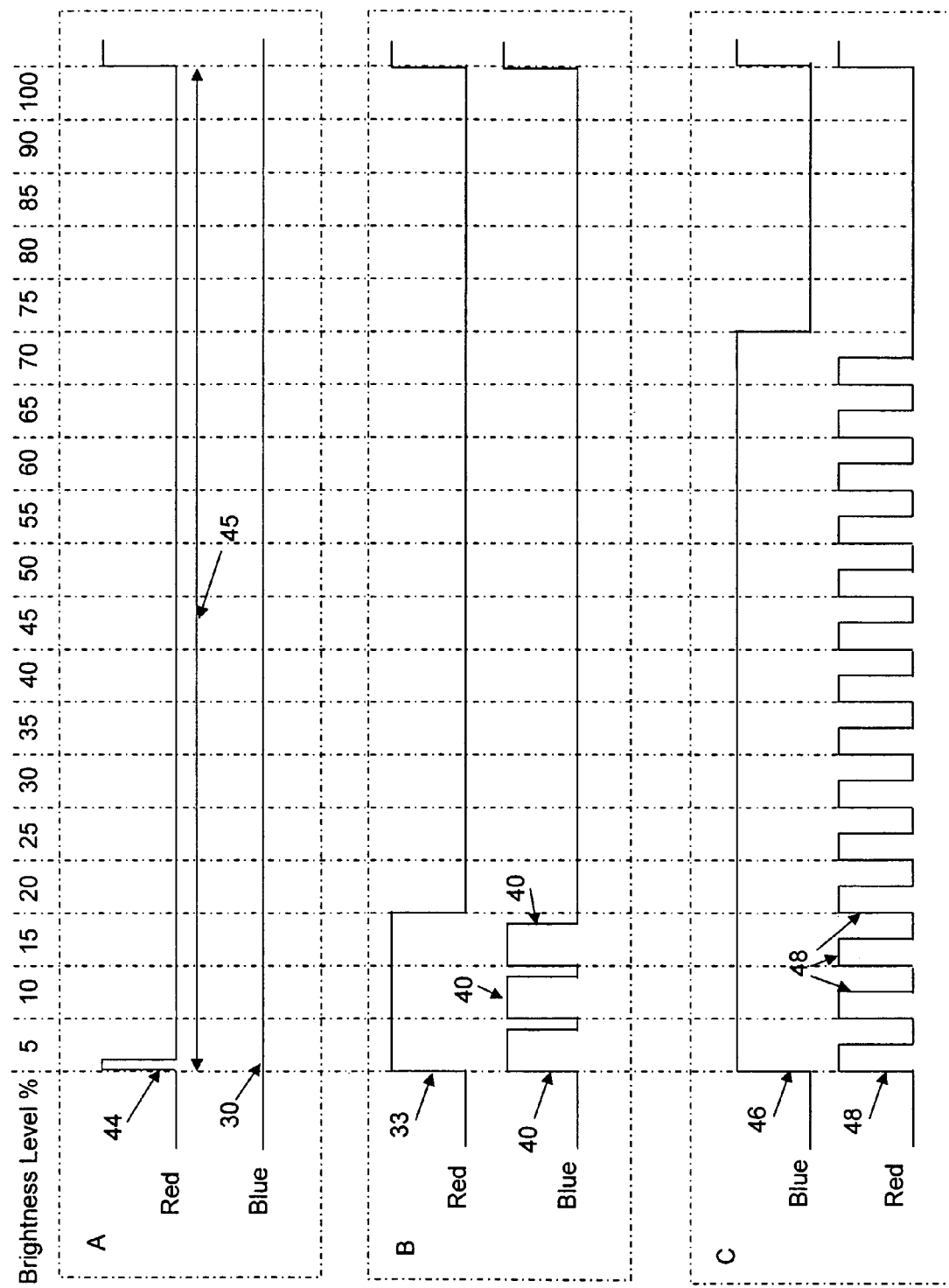
FIG. 3 illustrates sample modulated signal waveforms that provide different colors and brightness levels as perceived by the user of the relaxation device in accordance with an exemplary embodiment.

The relaxation device 170 allows a user to control the brightness produced by the LED arrangement 182 through brightness controls. Brightness is the attribute of visual sensation according to which an area appears to emit more or less light. As a result, brightness as a metric is subjective. In the exemplary embodiment, the brightness of the LED arrangement 182 can be adjusted in 20 steps. As a result, a single unit of brightness corresponds to 5% of the maximum level. The brightness of the selected color level is increased by repeating the selected color level during a pulse repetition interval 45 as shown in the examples of FIG. 3. As a result, a 100% brightness repeats the selected color level 20 times. Thus, adjustment of both the color and brightness controls generates different amplitude modulated signals that may comprise a single pulse in the form of a rectangular wave or a pulse train of rectangular waves during the pulse repetition interval 45 as shown in FIG. 3. In an exemplary embodiment, the pulse repetition interval is 10 ms. If the color and the brightness are both 100%, a 10 ms amplitude modulated signal is generated (20*500 µs).

For illustration, FIG. 3 provides several example amplitude modulated signals having different combined color and brightness levels. The brightness level corresponds to the number of repeated color levels that each comprise a 500 μs time duration. Thus, again, there are 20 brightness units in a 10 ms pulse repetition interval 45. Example A shows a single 62.5 μs pulse width rectangular wave signal 44 sent to one or both of the LEDs that emit the red light beam. One or both of the LEDs that emit the blue light beam are off 30. As a result, the color level of the LED emitting red light is 12.5% and the color level of the LED emitting blue light is 0%. The resulting combined color perceived by the user of the relaxation device 170 is red. As shown in example A, the brightness level is 5% because the selected color level is repeated only once during the 10 ms pulse repetition interval 45.

Example B shows a single 1500 μs pulse width signal 33 sent to one or both of the LEDs emitting the red light beam, and a pulse train comprised of three 437.5 μs pulse width signals 40 sent to one or both of the LEDs emitting the blue light beam. The combination of the 500 μs pulse width signal with the 437.5 μs pulse width signal 40 corresponds to color step 8 shown in FIG. 2. The LEDs emitting the red light beam have a color level of 100%, and the LEDs emitting the blue light beam have a color level of 87.5%. The resulting combined color perceived by the user of the relaxation device 170 is a slightly reddish purple. The brightness level emitted from the LEDs is 15% because the color level is repeated three times (3*5%) during the 10 ms pulse repetition interval 45.

Example C shows a single 7 ms pulse width signal 46 sent to one or both of the LEDs emitting blue light beam, and a pulse train comprised of fourteen 250 μs pulse width signals 48 sent to one or both of the LEDs emitting the red light beam. The combination of the 500 μs pulse width signal with the 250 μs pulse width signal 48 corresponds to color step 13. The LED emitting the blue light beam has a color level of 100%, and the LED emitting the red light beam has a color level of 50%. The resulting combined color perceived by the user of the relaxation device 170 is a bluish purple. The brightness level emitted from the LEDs is 70% because the color level is repeated fourteen times (14*5%) during the 10 ms pulse repetition interval 45.

The vibrancy of the light from the relaxation device 170 is driven by the lowest frequency component. In an exemplary embodiment, the lowest frequency component is 100 Hz which corresponds to a single pulse sent during the 10 ms pulse repetition interval 45. Light emitted with a frequency component of 100 Hz appears continuous to the human eye. Thus, regardless of the color level and the brightness level selected by the user, the light beam emitted toward the eye of the user appears continuous even though the LEDs may be physically flashing rapidly on and off as a function of the color and brightness signals that drive each LED and illustrated in FIG. 3.

As known to those skilled in the art, however, visibly flashing light at various frequencies induces different mood states in a person viewing the flashing light. These mood states are known as alpha, beta, delta, and theta. It is also recognized by those skilled in the art that flashing light at a frequency of 7.4 Hz and less contributes to a user entering a theta state. A frequency above 7.4 Hz contributes to the user entering an alpha state.

The relaxation device 170 provides a continuous mode wherein the light does not appear to flash even though the signals used to drive the LED arrangement 182 may cause the LEDs to quickly switch on and off in providing the selected color and brightness levels as illustrated in FIG. 3.

Thus, the continuous mode actually does not require a continuous signal because the light beams may appear continuous to the user because the frequency is greater than the frequency discernible to the human eye as flashing. In the continuous mode of operation, the signal selected by the user using the brightness controls and the color controls repeats in consecutive pulse repetition intervals during the treatment duration. Thus, for example, in continuous mode, color and brightness levels of example C in FIG. 3 would be repeated in each consecutive pulse repetition interval 45. Because the frequency is greater than 100 Hz, the color and brightness of the LEDs appears continuous to the human eye despite the use of a pulse train to drive the LED arrangement 182.

Figure 4:
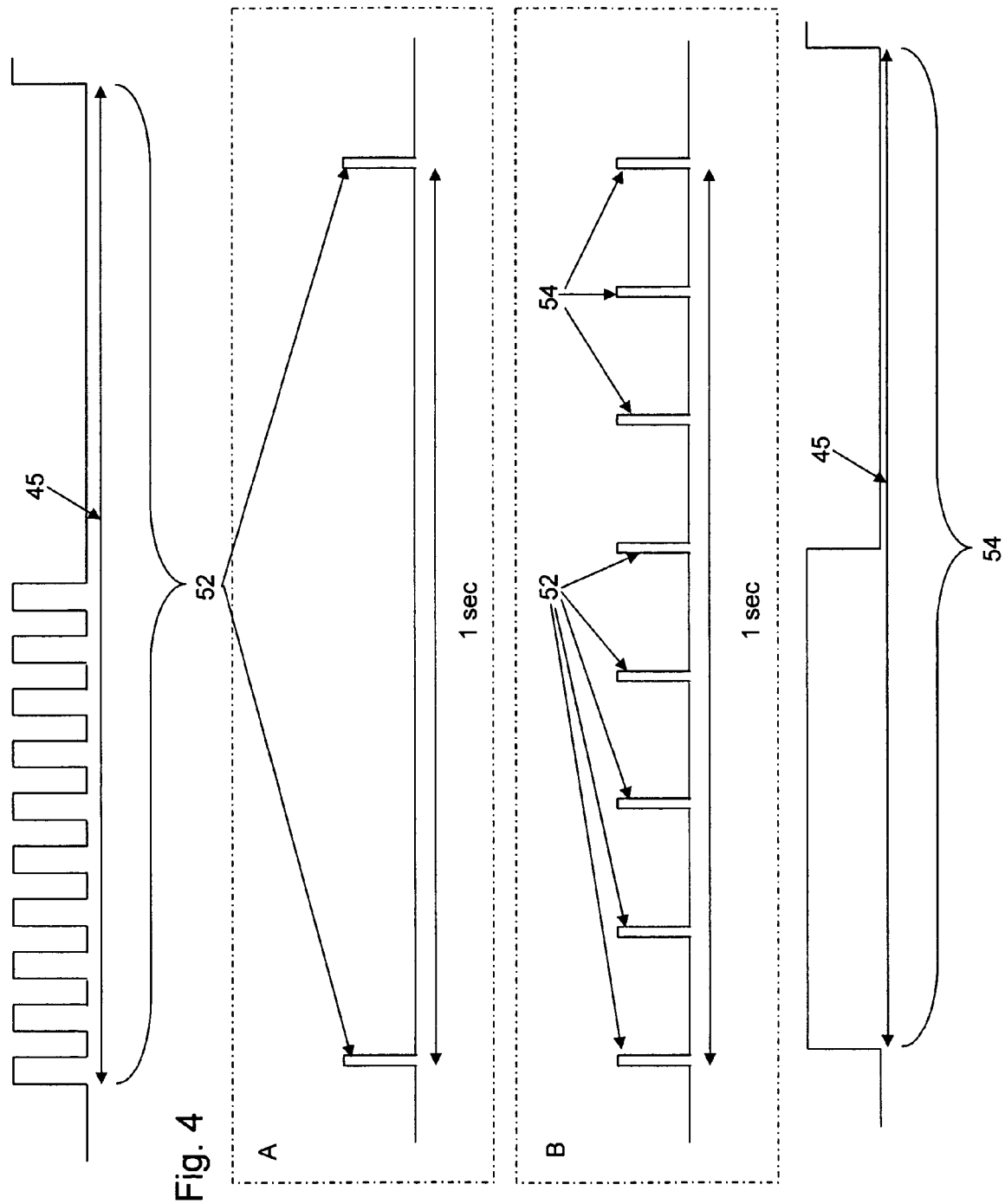
FIG. 4 illustrates sample waveforms that provide different flash frequencies for the relaxation device in accordance with an exemplary embodiment.

However, the user may want the light to visibly flash to induce a relaxation state. To provide for visually flashing light, the control electronics 184 of the relaxation device 170 generate signals that cause the LED arrangement 182 to perceptibly flash to a user. In an exemplary embodiment, the LED arrangement 182 flashs on and off at a frequency in the range from approximately 1 to approximately 7.5 Hz in eleven steps. In an exemplary embodiment, a single flash frequency controls the flash frequency for all of the LEDs of the LED arrangement 182. FIG. 4 illustrates two different flash frequency rates. Both example signals A and B are initially comprised of the same signal 52 that may be any signal creatable using the color and brightness controls as discussed above with reference to FIGS. 2 and 3. By adjusting the flash frequency control, the user selects a visual flash frequency that causes the signal 52 to turn on and off. As a result, the signal 52 selected by the user using the brightness controls and the color controls repeats during a cycle defined by the selected flash frequency. By periodically switching the signal 52 on and off, the light visually flashes. For example, a flash frequency of 1 Hz corresponds to the signal 52 driving the LED during a pulse repetition interval once per second as shown in Example A of FIG. 4. A flash frequency of 7 Hz corresponds to the signal 52 driving the LED during the pulse repetition interval seven times per second. As shown in Example B of FIG. 4, the user selects a flash frequency of 7 Hz and adjusts the color controls and the brightness controls initially to generate signal 52. However, after five cycles or approximately 0.7 seconds, the user adjusts the color control to generate signal 54 (the brightness level remains at 50%) at the 7 Hz flash frequency. If a user instead selects the continuous mode, the signal repeats in every pulse repetition interval resulting in at least a 100 Hz flash frequency that is not detectable by the human eye, and thus, appears continuous.

Figure 5:
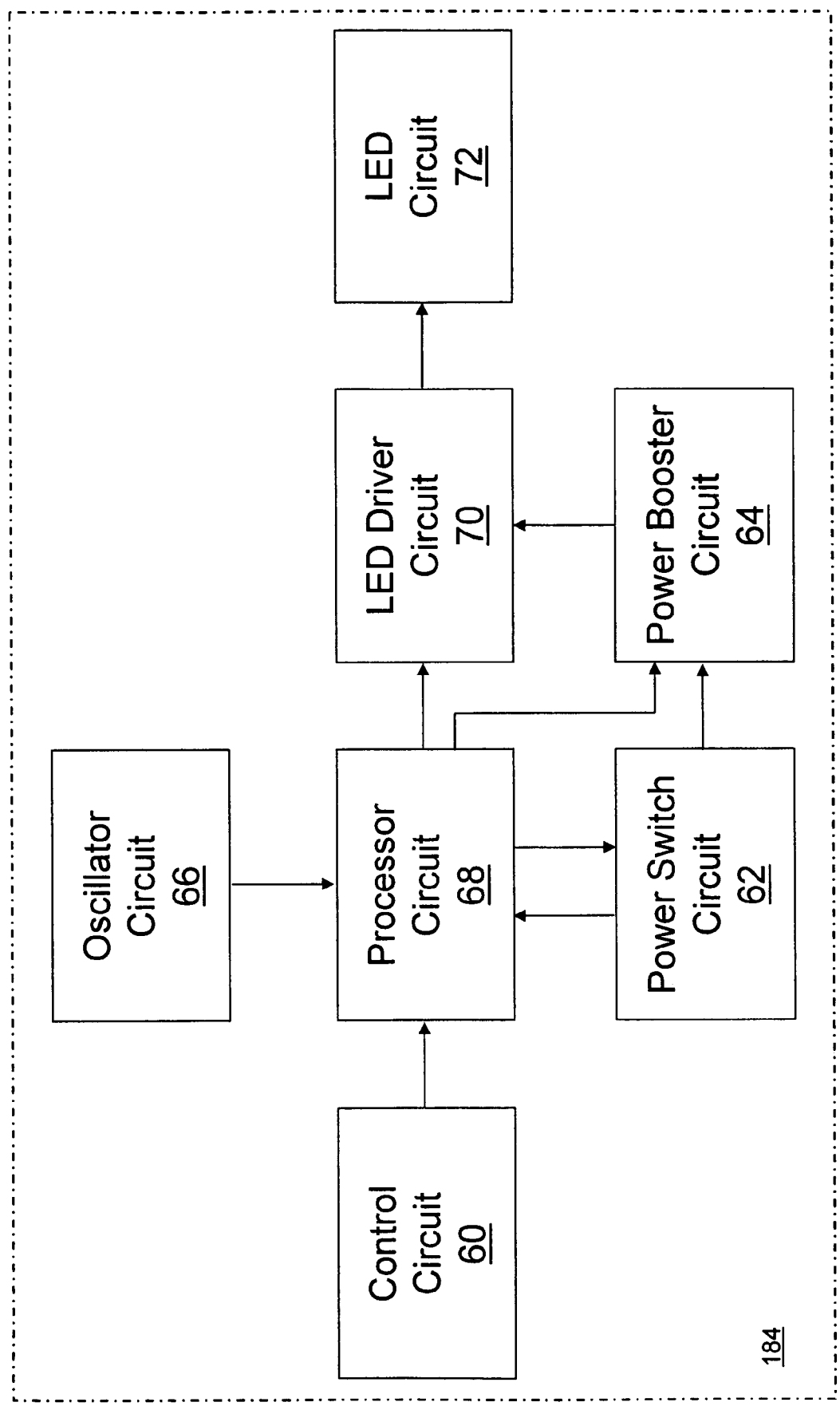
FIG. 5 is a block diagram of the processing flow for the control electronics of the relaxation device in accordance with an exemplary embodiment.

With reference to FIG. 5, the control electronics 184 are shown in block diagram form to capture the high level functionality of the circuitry. The control electronics 184 comprise a control circuit 60, a power switch circuit 62, a power booster circuit 64, an oscillator circuit 66, a processor circuit 68, an LED driver circuit 70, and an LED circuit 72.

Figure 6:
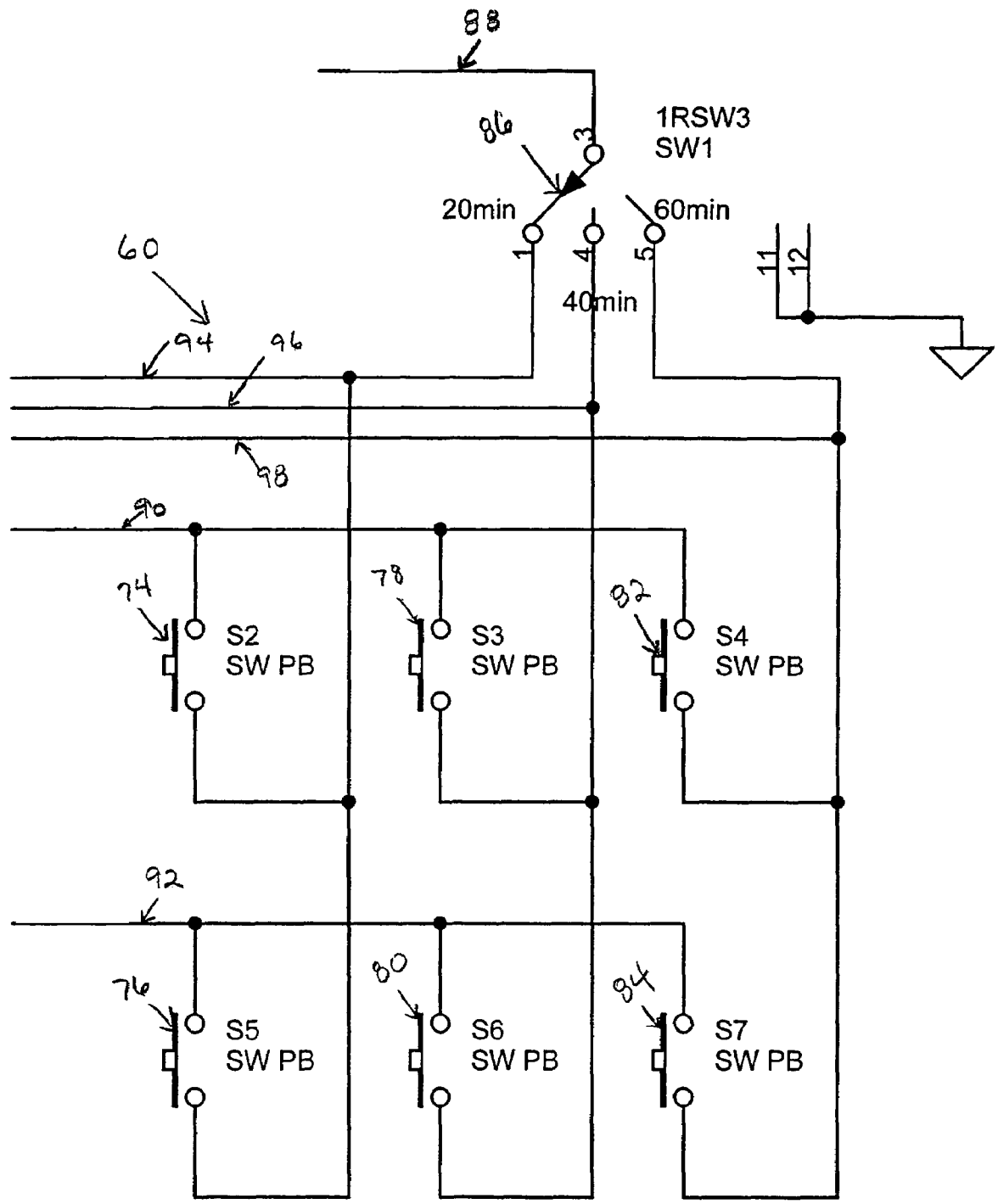
FIG. 6 is a detailed schematic diagram of a control circuit of the relaxation device in accordance with an exemplary embodiment.

In addition to selecting the color, the brightness, and the flash frequency, the user may select the duration of the treatment. Of course, the user may end the treatment at any time, but the relaxation device 170 also provides for an automatic shut off based on a timer. Through experimentation and testing, the inventor has determined that by flashing a light beam into the eye of a user for a time duration equal to, or exceeding twenty minutes, beta endorphins are increased in the bloodstream as well as in the fluid surrounding the user's brain. These beta endorphins have been recognized to relate to a relaxation state or mood of a person. As shown in FIG. 6, in an exemplary embodiment, the duration of treatment control 86 may allow a selection in the range from 20 minutes to 60 minutes in three steps. Thus, a user may select a duration of treatment of 20, 40, or 60 minutes. Any duration of treatment time may be implemented in alternative embodiments. The processor circuit 68 sends a signal to the power switch circuit 62 that shuts off the relaxation device 170 when the selected time duration is reached.

Control circuit 60 provides pushbuttons and switches for the user to control the color, the brightness, the flashing frequency, and the time duration of the relaxation session. FIG. 6 shows an exemplary embodiment of the control circuit 60. Switch 82 controls the color of the LEDs emitting red light beams. Switch 84 controls the color of the LEDs emitting blue light beams. Pushbutton 74 allows the user to increase the brightness of the LED arrangement 182. Pushbutton 76 allows the user to decrease the brightness of the LED arrangement 182. The last value selected for the brightness may be saved in the memory of a processor 130 (shown with reference to FIG. 9). Pushbutton 78 allows the user to increase the flash frequency of the LED arrangement 182. Pushbutton 80 allows the user to decrease the flash frequency of the LED arrangement 182. The last value selected for the flash frequency may be saved in the memory of the processor 130. Switch 86 allows the user to select the time duration. Signal lines 88, 90, 92, 94, 96, 98 provide inputs to the processor circuit 68.

Figure 7:
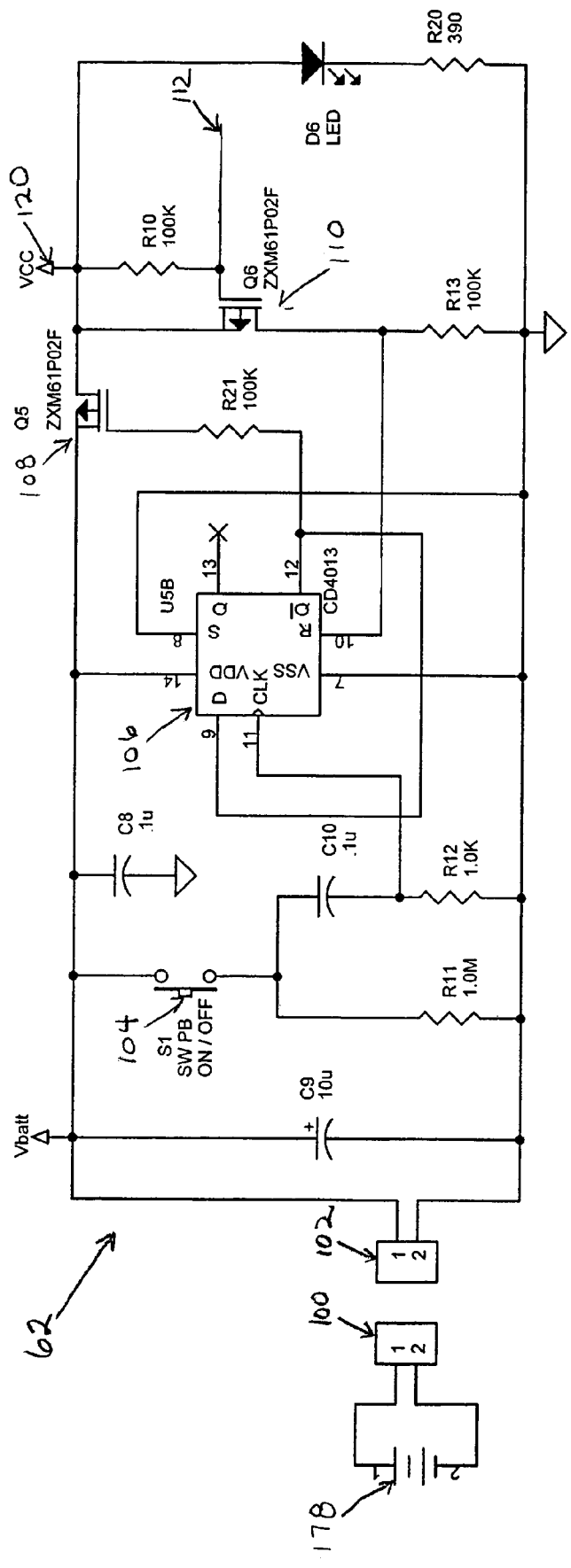
FIG. 7 is a detailed schematic diagram of a power switch circuit of the relaxation device in accordance with an exemplary embodiment.

As shown in the exemplary embodiment of FIG. 7, the power switch circuit 62 connects to the power source 178 through connectors 100 and 102. On/off switch 104 allows the user to turn on or off the relaxation device 170. Flip-flop 106 toggles the power circuit on and off based on the setting of switch 104. In an exemplary embodiment, the flip-flop 106 may be a CD4013 Dual D-Type Flip-Flop produced by Fairchild Seminconductor™. Only one half of the dual flip-flop 106 is used as shown in FIG. 7. Additionally, the exemplary embodiment includes a first Metal Oxide Semiconductor Field-Effect Transistor (MOSFET) 108 to provide a low on resistance and a fast switching speed. Similarly, a second MOSFET 110 provides a fast switching speed when the duration timer signal 112 connected to the processor circuit 68 switches high resetting the flip-flop 106.

Figure 8:
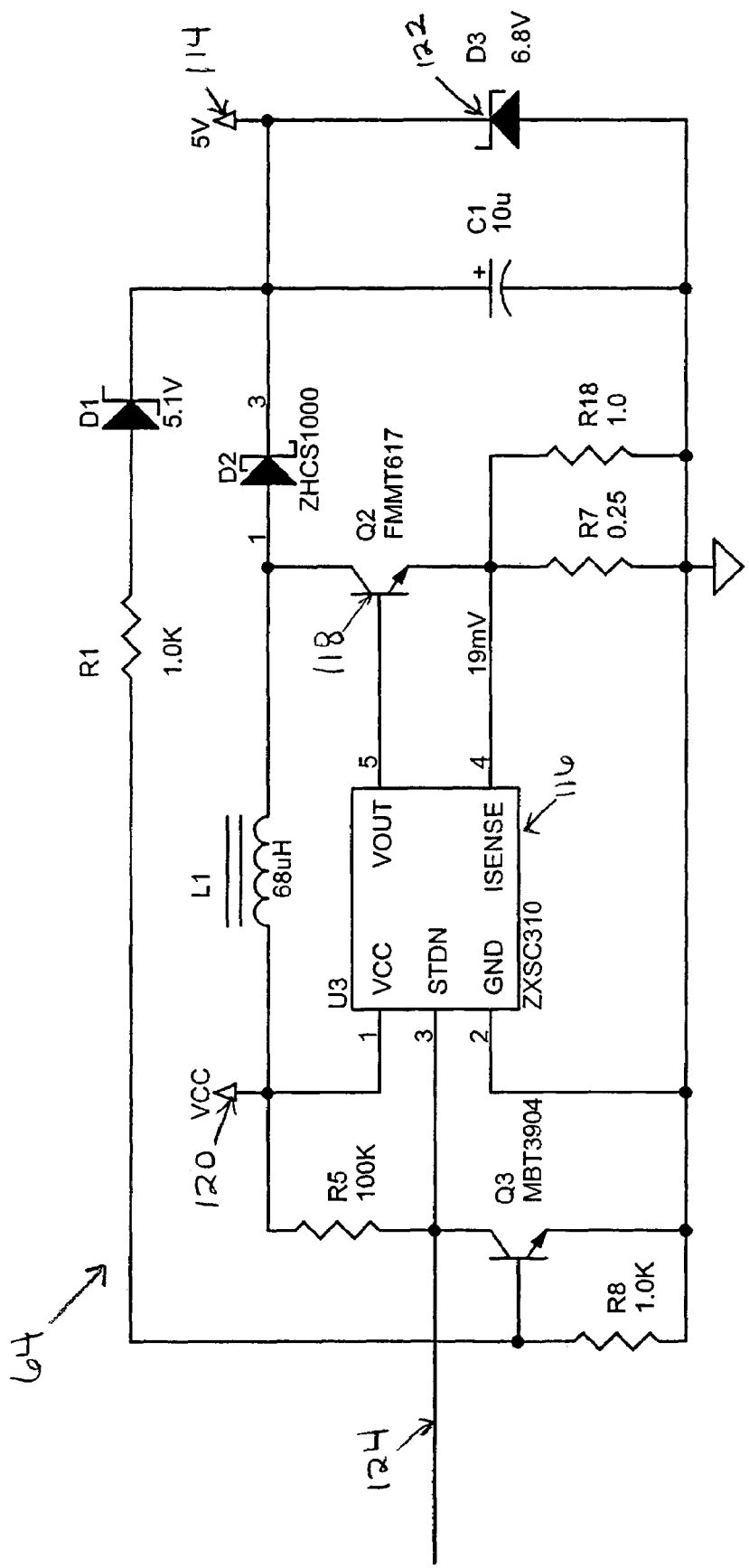
FIG. 8 is a detailed schematic diagram of a power booster circuit of the relaxation device in accordance with an exemplary embodiment.

As related previously, the relaxation device 170 may be powered by two AA batteries. The LED arrangement 182, however, in the exemplary embodiment, may need more than 3 V. Thus, a power booster circuit 64 is provided in an exemplary embodiment as shown in FIG. 8. The power booster circuit 64 generates 5 V for the LED arrangement 182 at line 114. To maintain the stability of the color and the brightness of the LEDs, the 5 V output 114 from the power booster circuit may be stabilized independent of the battery voltage as known to those skilled in the art.

In the exemplary embodiment of FIG. 8, the DC-DC controller 116 is a single or multi cell LED driver capable of driving serial or parallel LEDs. The DC-DC controller 116 drives an external Zetex switching transistor 118 with a very low saturation resistance. The power switch circuit 62 supplies the external input voltage 120 to the DC-DC controller 116. The Zener diode 122 clamps the output voltage 114 at 6.8 V in an output open circuit configuration. Thus, Zener diode 122 provides protection when the LED arrangement 182 is not connected to the output voltage 114. The processor circuit 68 provides the serial input that generates the shutdown signal 122 that enables or disables the power booster circuit 64.

Figure 9:
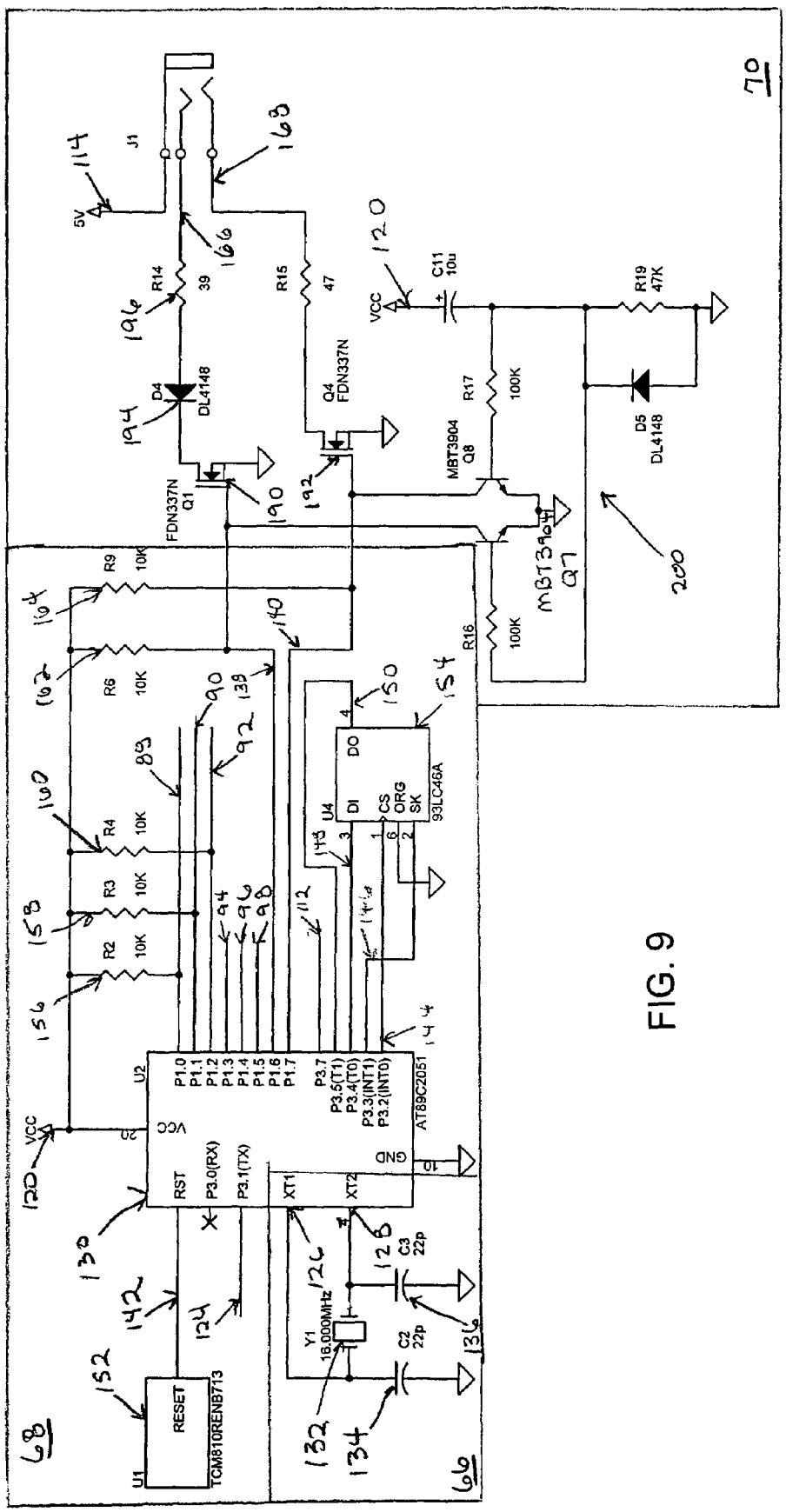
FIG. 9 is a detailed schematic diagram of an oscillator circuit, a processor circuit, and an Light Emitting Diode (LED) driver circuit for the relaxation device in accordance with an exemplary embodiment.

With reference to FIG. 9, an exemplary embodiment of oscillator circuit 66 is shown. An oscillator circuit 66 produces a repetitive electronic signal, often a sine wave or a square or a rectangular wave at a specified center frequency. Pins XT1 126 and XT2 128 of the processor 130 are the input and output, respectively, of an inverting amplifier that can be configured for use as an on-chip oscillator. Oscillator timing component 132 may be a quartz crystal or a ceramic resonator. If capacitors 134, 136 to ground are not included, a quartz crystal is preferred. In an exemplary embodiment the oscillator timing component for the processor 130 provides a 16 MHz reference timing signal.

The processor 130 of the processor circuit 68 generates the appropriate control signals for the LED arrangement 182 and receives commands from the control circuit 60. In an exemplary embodiment as shown in FIG. 9, the processor 130 comprises an 8-bit microcontroller with 2K Bytes of Flash memory of the type AT89C2051 manufactured by Atmel®.

The AT89C2051 is a low voltage, high performance CMOS 8-bit microcomputer with programmable and erasable read only memory. The device is compatible with the industry standard MCS-51 instruction set. Pin P3.1 124 is a serial output port that connects to the power booster circuit 64 shutdown input. Pin P3.7 112 connects to the power switch circuit 62 and provides the shutoff signal when the time duration selected by the user using the time duration control 86 is reached. Pins P1.0 to P1.5 88, 90, 92, 94, 96, 98 connect to the control switches from the control circuit 60. Pin P1.6 138 connects to the LED driver circuit 70 that drives the LEDs emitting red light beams. Pin P1.7 140 connects to the LED driver circuit 70 that drives the LEDs emitting blue light beams.

In an exemplary embodiment, the processor 130 reset pin 142 connects to a 3-pin microcontroller 152 that monitors the input voltage and provides a high reset signal to the processor 130. An example microcontroller 152 is TCM810RENB713 manufactured by Microchip Technology, Inc. All of the input and output pins of the processor 130 are reset to "1" as soon as the reset pin 142 goes high.

In an exemplary embodiment, the processor 130 input/output pins P3.2 144, P3.3 146, P3.4 148, and P3.5 150 connect to a serial Electrically Erasable Programmable Read Only Memory (EEPROM) 154. An example EEPROM 154 is the 93LC46A manufactured by Microchip Technology, Inc. The EEPROM 154 provides 8-bit communication with processor 130. The EEPROM 154 also provides low power, nonvolatile memory for the processor 130. Non-volatile means the data remains in the EEPROM 154 even when power is removed from the device. Data is written to the EEPROM 154 using processor 130 pin P3.4 148. Data is read from the EEPROM 154 using processor 130 pin P3.5 150. Processor 130 pin 3.3 146 provides the clock input to the EEPROM 154. Processor 130 pin 3.2 144 provides the chip select input to the EEPROM 154. Resistors 156, 158, 160, 162, 164 pull up open collector outputs at processor 130 pins P1.0 88, P1.1 90, P1.2 92, P1.6 138, and P1.7 140.

In an exemplary embodiment, the processor 130 may not provide enough current to drive the LEDs. As a result, the LED driver circuit 70 may be used to supply the proper current for each LED. A first MOSFET 190 connects to line 166 of the LED circuit 72 under the control of the processor 130 at the pin P1.6 138. A second MOSFET 192 connects to line 168 of the LED circuit 72 under the control of the processor 130 at the pin P1.7 140. The current that drives the LEDs emitting red light is controlled by a diode 194 in series with a resistor 196. The current that drives the LEDs emitting blue light is controlled by a resistor 198. In an exemplary embodiment, the LED driver circuit 70 includes a circuit 200 that disables the LED driver circuit 70 during the power on of the relaxation device 170 to prevent the user's eyes from receiving a strong initial flash of light from the LED arrangement 182. Thus, the processor may be disabled during an initial time period that acts as the "reset time" for the relaxation device 170. In an exemplary embodiment, the reset time is 300 milliseconds.

Figure 10:
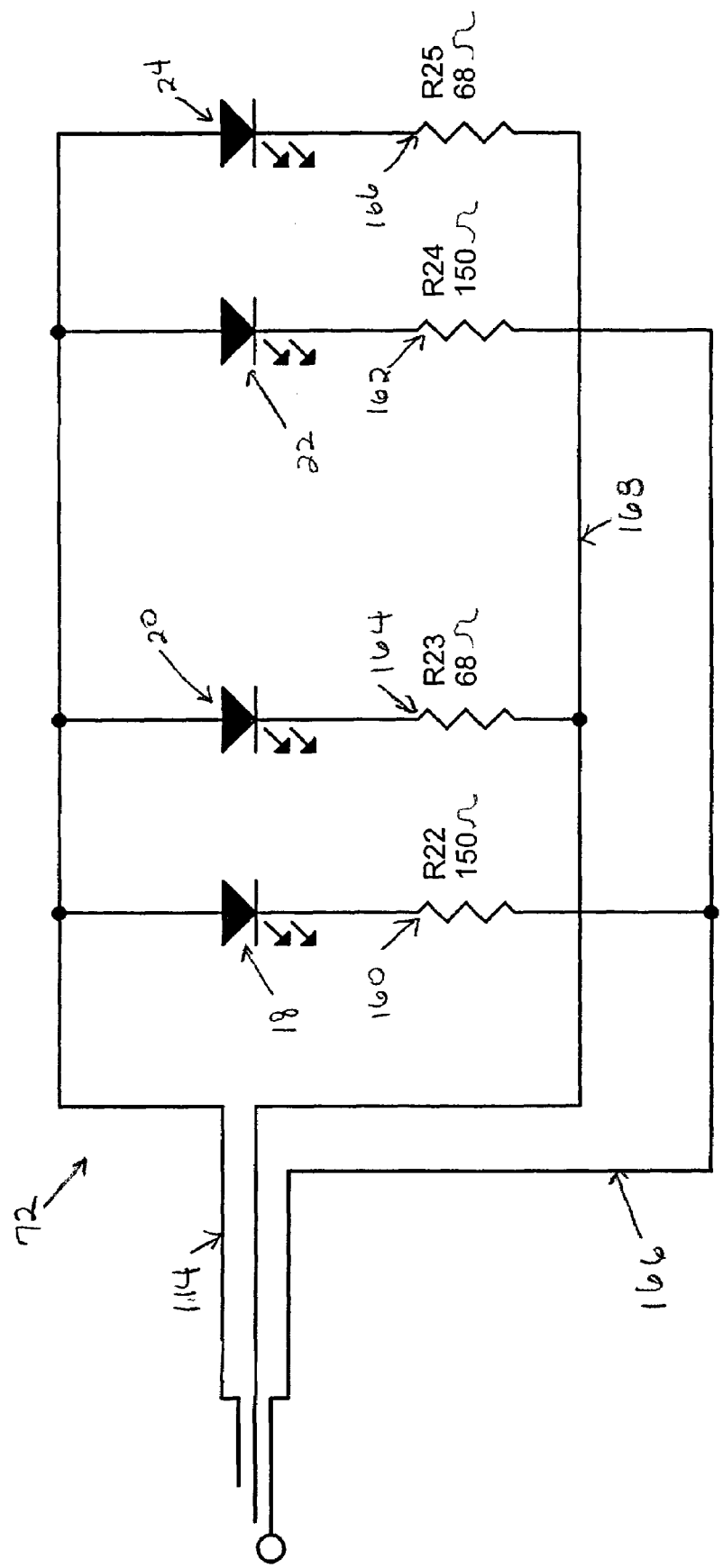
FIG. 10 is a detailed schematic diagram of an LED circuit of the relaxation device in accordance with an exemplary embodiment.

To limit the current flowing through the LED arrangement 182 to a safe value, each LED should have a resistor in series with the LED. Additionally, it is sometimes difficult to match even identical LEDs in brightness. The recommended method of matching the brightness of LEDs is by driving each LED with the same current. However, this approach can be expensive. As a result, most applications use a fixed bias voltage and a ballast resistor in series with each LED. In the exemplary embodiment of FIG. 10, line 114 of LED circuit 72 connects to the stable 5 V power source provided by the power booster circuit 64, and thus, provides the fixed bias voltage. Line 166 connects to the processor 130 at the pin P1.6 138 through the LED driver circuit 70. The pulse width modulated signal transmitted on line 166 and defined by processor 130 based on user selection of the color, brightness, and flash frequency drives an LED 18 and an LED 22 that emit red light beams. Line 168 connects to the processor 130 at the pin P1.7 140 through the LED driver circuit 70. The pulse width modulated signal transmitted on line 168 and defined by processor 130 based on user selection of the color, brightness, and flash frequency drives an LED 20 and an LED 24 that emit blue light beams. Ballast resistors 160 and 162 for the LEDs 18, 22 emitting red light beams are preferably 150 ohms. Ballast resistors 164 and 166 for the LEDs 20, 24 emitting blue light beams are preferably 68 ohms.

The ballast resistors are different based on the different sensitivities of the LEDs emitting red light beams as compared to the LEDs emitting blue light beams.

The functionality discussed herein may be implemented by different circuitry than shown as known to those skilled in the art. Additionally, the functionality may be split into greater or fewer components than shown without deviating from the spirit of the invention. It is understood that the invention is not confined to the particular embodiments set forth herein as illustrative, but embraces all such forms thereof as come within the scope of the following claims:

What is claimed is:

1. A method of inducing a relaxation state in a user, the method comprising:

receiving a first input from a first color control, wherein the first color control provides user selection of the pulse width of a first rectangular wave;

receiving a second input from a second color control, wherein the second color control provides user selection of the pulse width of a second rectangular wave;

receiving a second input from a brightness control, wherein the brightness control provides user variation of the repetition rate of the first rectangular wave thereby forming a first amplitude modulated signal and provides user variation of the repetition rate of the second rectangular wave thereby forming a second amplitude modulated signal;

emitting a first light beam from a first light source toward a first eye of a user, the first light beam having a first color and generated from the first amplitude modulated signal;

emitting, simultaneous with the first light beam, a second light beam from a first light source toward the first eye of the user, the second light beam having a second color and generated from the second amplitude modulated signal, wherein the second color is different from the first color; and providing a first combined color perceived by the first eye of the user from the first light beam and the second light beam wherein the first color control and the second color control provide user control of the first combined color, and the brightness control provides user control of the brightness of the first combined color.

2. The method of claim 1, wherein the separation distance between the first light source and the second light source is in the range of approximately 3 to approximately 4 millimeters.

3. The method of claim 1, wherein the first color is red and the second color is blue.

4. The method of claim 1, wherein the pulse width of the first rectangular wave is in the range from approximately 62.5 microseconds to approximately 500 microseconds.

5. The method of claim 1, wherein the pulse width of the second rectangular wave is in the range from approximately 62.5 microseconds to approximately 500 microseconds.

6. The method of claim 1, further comprising:

emitting a third light beam from a third light source toward a second eye of the user, the third light beam having a third color and generated from the first amplitude modulated signal;

emitting, simultaneous with the third light beam, a fourth light beam from a fourth light source toward the second eye of the user, the fourth light beam having a fourth color and generated from the second amplitude modulated signal, wherein the fourth color is different from the third color; and providing a second combined color perceived by the second eye of the user from the third light beam and the fourth light beam wherein the first color control and the second color control provide user control of the second combined color, and the brightness control provides user control of the brightness of the second combined color.

7. The method of claim 6, wherein the separation distance between the third light source and the fourth light source is in the range of approximately 3 to approximately 4 millimeters.

8. The method of claim 6, wherein the third color is red and the fourth color is blue.

* * * * *

UNITED STATES PATENT AND TRADEMARK OFFICE
CERTIFICATE OF CORRECTION

PATENT NO. : 7,645,226 B2
APPLICATION NO. : 10/988204
DATED : January 12, 2010
INVENTOR(S) : Shealy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1461 days.

Signed and Sealed this

Sixteenth Day of November, 2010

David J. Kappos
*Director of the United States Patent and Trademark Office*